(12) United States Patent
Shim et al.

(10) Patent No.: US 8,590,206 B2
(45) Date of Patent: Nov. 26, 2013

(54) METHOD AND SYSTEM FOR STERILIZATION OF THE SOIL FOR GROWING KOREAN GINSENG BY USING AN ELECTRON BEAM AND SYSTEM OF GROWING KOREAN GINSENG USING AN ELECTRON BEAM STERILIZATION

(75) Inventors: Hyeon-Jea Shim, Jeollabuk-do (KR); Min-Young Kang, Gyeonggi-do (KR); Yong-Dol Shin, Jeollabuk-do (KR)

(73) Assignee: GBioMix Co., Ltd., Jeollabuk-do (KP)

( * ) Notice: Subject to any disclaimer, the term of this patent is extended or adjusted under 35 U.S.C. 154(b) by 243 days.

(21) Appl. No.: 12/963,811

(22) Filed: Dec. 9, 2010

(65) Prior Publication Data
US 2012/0144739 A1 Jun. 14, 2012

(51) Int. Cl.
*A01G 31/02* (2006.01)
(52) U.S. Cl.
USPC .................................................. 47/65
(58) Field of Classification Search
USPC .............. 47/1.01 P, 1.01 R, 58.1 SC, 58.1 LS
See application file for complete search history.

(56) References Cited

U.S. PATENT DOCUMENTS

| 3,771,258 A * | 11/1973 | Charney ............................. 47/65 |
| 5,425,923 A * | 6/1995 | Swisher et al. ................ 422/168 |
| 5,779,813 A * | 7/1998 | Plunkett ........................... 134/12 |
| 2006/0150508 A1* | 7/2006 | Whitcomb et al. ................ 47/86 |
| 2006/0156626 A1* | 7/2006 | Seaman ............................ 47/79 |
| 2008/0148633 A1* | 6/2008 | Singh ................................ 47/65 |
| 2009/0013596 A1* | 1/2009 | Wang ................................ 47/17 |
| 2009/0199470 A1* | 8/2009 | Capen et al. ............. 47/58.1 LS |
| 2010/0285054 A1* | 11/2010 | De Souza et al. ........ 424/195.15 |

FOREIGN PATENT DOCUMENTS

JP 2003145128 A * 5/2003

\* cited by examiner

*Primary Examiner* — Monica Williams
(74) *Attorney, Agent, or Firm* — Patterson Thuente Pedersen, P.A.

(57) ABSTRACT

The present invention relates to a method and system for sterilizing the soil for growing Korean ginseng by using an electron beam, which eliminates fungi harmful to ginseng's growth and development, and also relates to a system including: a conveyor which transfers the soil for growing Korean ginseng; a soil supplier which loads a predetermined amount of soil onto the conveyor to a predetermined height; an electron beam irradiator which applies electron beam to the soil for growing Korean ginseng being transferred by the conveyor to eliminate fungi contained in the soil for growing Korean ginseng; and an antagonistic rhizobacteria supplier which adds antagonistic rhizobacteria to the sterilized soil.

8 Claims, 5 Drawing Sheets

METHOD AND SYSTEM FOR STERILIZATION OF THE SOIL FOR GROWING KOREAN GINSENG BY USING AN ELECTRON BEAM AND SYSTEM OF GROWING KOREAN GINSENG USING AN ELECTRON BEAM STERILIZATION

BACKGROUND OF THE INVENTION

The present invention relates to a method and system for sterilization of the soil for growing Korean ginseng by using an electron beam and is an improved growing system for Korean ginseng. More particularly, first inorganic matter including iron (Fe) and aluminum (Al) is removed from the soil for growing Korean ginseng through the method and system, and then electron beam is applied to the soil by the electron beam irradiator, to sterilize diverse harmful fungi in it. Ginseng beds are built with the sterilized soil in a ginseng field. The present invention allows mass production of organically grown Korean ginseng.

The sterilized soil can be also filled in a rectangular box called ginseng-field-module instead of a ginseng bed. A ginseng field can be constructed with these ginseng-field-modules in a straight line or in multi-layer form considering geographical condition in the shade of solar cell panel in a solar cell yard or in the shade of artificial device.

These modules bring new opportunity that Korean ginseng can be cultivated in a same condition without influence from climatic changes.

As is well known, ginseng, in particular, Korean ginseng (Panax ginseng C. A. Meyer), is a special crop that is widely grown in Korea as a medicinal plant. Generally, Korean ginseng is harvested four to six years after it is planted.

In terms of medicinal effects and price, six-year-old Korean ginseng is far better than its counterparts of other ages. Thus, it is desirable to harvest Korean ginseng after grown for six years. In many cases, however, Korean ginseng has to be harvested before it becomes six years old, usually, when it is four years old, due to various fungi (such as *cylindrocarpon destructans, fusarium solani, erwinia carotovora* and *pseudomonas fluorescens*) which are created and parasitized as it grows.

In addition, these harmful fungi still reside in the soil of a ginseng field even after ginseng is harvested. Therefore, the ginseng field cannot be reused to grow ginseng continuously and repeatedly.

For these reasons, the soil of the ginseng field must be fumigated before Korean ginseng is repeatedly planted, or crops must be rotated on the soil for ten years. However, in the case of fumigation, since ammonia-based nitrogen is created as chloropicrin decomposes in the soil, the nitrogen content of the soil is increased, which is highly likely to cause physiological disorders in ginseng. In the case of crop rotation, the land where Korean ginseng can be cultivated is limited. In particular, when Korean ginseng is planted in a paddy field, chemical fertilizers left in the paddy field can cause rusty root of ginseng. Thus, ryes can be planted in the paddy field to absorb inorganic nutrients remaining in the paddy field before planting ginseng.

Furthermore, it is very difficult to prevent the roots of Korean ginseng from rotting due to fungi (especially *cylindrocarpon destructans*) or to early detect the rotting of the roots. Accordingly, it is not easy to produce high-quality six-year-old Korean ginseng. Even if six-year-old Korean ginseng is successfully produced from a ginseng field, the ginseng field cannot be reused to continuously grow Korean ginseng due to fungi that exist in the soil of the ginseng field.

Photosynthesis of ginseng stops over 28° C. due to its physiological characteristics.

Therefore a sun shading equipment is required to block sunlight up to 88% and to maintain an optimal temperature of ginseng field between 20 to 27° C. in summer.

Such a sun shading equipment causes raise of maintenance costs, so that it weakens the competitiveness of Korean ginseng cultivation.

Especially when we consider the serious climate changes of the Earth, it is anticipated that we will encounter more difficulty in ginseng cultivation and severe damage caused by global warming.

Besides, if we continuously use a traditional method of ginseng cultivation, it is difficult to produce uniform high-quality ginseng in large quantities, by reason that the method is based on manual work and traditional sun shading equipment is far from automating. Due to lack of technology such as a sun shading equipment for automating system of ginseng cultivation, we only can depend on practical experience.

Actually it is impossible to automate ginseng field because of sun shading equipment' structure and its small space.

And until now there has been also no research to automate such a ginseng field or to use a shade space made at the back side of solar cell panel in a solar cell yard.

SUMMARY OF THE INVENTION

Aspects of the present invention provide a method and apparatus for sterilizing the soil for growing Korean ginseng by using an electron beam, not only in which a high-energy electron beam is applied to the soil of a first cultivated ginseng field or a continuously cultivated ginseng field to eliminate fungi harmful to ginseng and antagonistic rhizobacteria are added to the soil, so that we can prevent the roots of Korean ginseng from being infected with the fungi and ultimately produce high-quality organic Korean ginseng, but also in which, after six-year-old ginseng is harvested from the soil, we apply the electron beam to the soil to eliminate fungi and then add antagonistic rhizobacteria to the soil to continuously cultivate high-quality organic Korean ginseng in the same soil.

Aspects of the present invention also provide a method and system for sterilizing the soil for growing Korean ginseng by using an electron beam, in which inorganic matter harmful to ginseng are removed from the soil. After this, additionally, antagonistic rhizobacteria helpful for the growth of ginseng are added to the soil in order to provide optimal soil for growing ginseng and thus to produce higher-quality ginseng.

Aspects of the present invention also provide a method and apparatus for sterilizing the soil for growing Korean ginseng by using an electron beam, in which it is possible to continuously and organically grow high-quality Korean ginseng in the same soil in order to maximize the efficiency of land use and to increase the income of farming households.

Also the present invention provides one solution to grow uniform high-quality ginseng using ginseng-field-modules which can help ginseng grow uninfluenced from climatic influence.

This ginseng-field-module can be easily arranged and assembled through coupling pipes and a rack in a row or layer upon layer considering geographical conditions of a solar cell yard or a typical ginseng field.

According to an aspect of the present invention, there is provided a method of sterilizing the soil for growing Korean ginseng by eliminating fungi, which are contained in the soil for growing ginseng and cause roots of ginseng to rot. The method includes transferring the soil loaded to a predetermined height on a conveyor moving at a predetermined speed and applying an electron beam to the soil for growing Korean ginseng in order to eliminate fungi contained in the soil for growing ginseng.

The soil for growing Korean ginseng will be passed through an electromagnet to remove inorganic matter including iron (Fe) and aluminum (Al) from the soil for growing Korean ginseng before the soil for growing Korean ginseng is exposed to the electron beam.

The soil for growing Korean ginseng is loaded to a height of 5 cm or below 5 cm on a conveyor and then exposed to at least 10 kGy of electron beam irradiation.

Antagonistic rhizobacteria is supplied to the soil for growing Korean ginseng after the soil for growing Korean ginseng is exposed to the electron beam.

The antagonistic rhizobacteria can include a mixture of one or more of dominant bacteria, aseron and antagonistic rhizobacteria. And materials to be used as strains of the antagonistic rhizobacteria can include a mixture of one or more of sawdust, rice bran, sesame dregs, powdered bones, fish meal, wheat bran, zeolite, glucose, CaO and $Na_2CO_3$.

According to another aspect of the present invention, there is provided a system for sterilizing the soil for growing Korean ginseng by using an electron beam. The system includes: a soil supplier which prepares and screens the soil for growing Korean ginseng and supplies the screened soil for growing Korean ginseng in predetermined amounts; a main conveyor which transfers the soil for growing Korean ginseng supplied by the soil supplier at a predetermined speed; and an electron beam irradiator which applies an electron beam to the soil for growing Korean ginseng being transferred by the main conveyor to eliminate fungi contained in the soil for growing Korean ginseng.

The soil supplier includes an electromagnet which removes inorganic matter from the soil for growing Korean ginseng.

The system further includes an antagonistic rhizobacteria supplier which is disposed at an end of the main conveyor behind the electron beam irradiator and which adds a mixture of one or more of antagonistic rhizobacteria, dominant bacteria and aseron to the sterilized soil for growing Korean ginseng.

The electron beam irradiator must comprise a safety cover wall which prevents the leakage of the electron beam.

The system further includes: a salt removing tank which is disposed in front of the soil supplier, removes salts from the soil for growing Korean ginseng, has a drain in a lower part thereof, and is filled with the soil for growing Korean ginseng; and a sprinkler which is disposed above the salt removing tank and sprays water over the soil for growing Korean ginseng.

And the system consists of following units: another conveyor that is arranged at the end of main conveyor which carries the sterilized and mixed with antagonistic rhizobacteria soil to the ginseng-field-module; ginseng-field-module without cover; guide rail on which the ginseng-field-module filled of sterilized soil can be transported to a shade space made at the back side of solar cell panels in a solar cell yard or another shade space made artificially in a ginseng field; and solar cell panel.

This now, as we mentioned earlier, ginseng-field-modules can be assembled in a row or layer upon layer through coupling pipes and a rack. And at the upper top of the ginseng-field -module is installed a pipe that has many small holes to supply water or nourishment. It is also desirable that temperature and humidity sensor are installed inside of the ginseng-field-module.

And it is also desirable that blue and red LEDs are installed above the ginseng -field-module or on the frame of solar cell equipment, to activate ginseng's photosynthesis at cloudy, bad or rainy weather.

In addition, at the side of the above-mentioned ginseng-field-module is installed a fan in order to control the temperature and ventilation of the ginseng-field-modules.

DESCRIPTION OF THE PREFERRED EMBODIMENT

Hereinafter, an example about a method and system for sterilizing the soil for growing Korean ginseng will be described in detail with reference to the attached drawings according to exemplary embodiments of the present invention.

The 1st example of this patent is a method and system for sterilizing the soil for growing Korean ginseng irradiating electron beam to the soil.

Figure 1:
FIG. 1 and FIG. 2 show a schematic diagram for explaining a process of sterilizing the soil for growing Korean ginseng by using an electron beam according to an exemplary 1st example.

FIG. 1 is a schematic diagram for explaining a plurality of operations included in a method of sterilizing the soil for growing Korean ginseng according to an exemplary embodiment of the present invention.

Referring to FIG. 1, the method of sterilizing the soil for growing Korean ginseng according to the present embodiment essentially includes operation S20 in which an electron beam is applied to soil for growing Korean ginseng in order to eliminate harmful fungi in the soil.

As described above, typical examples of harmful fungi including *cylindrocarpon destructans* that cause ginseng roots to rot are *fusarium solani, erwinia carotovora*, and *pseudomonas flurescens*. These harmful fungi can be eliminated by electron beam irradiation.

According to the present invention, when an electron beam is applied to the soil, harmful fungi are killed in a collision with the continuous flow of high energy electrons produced by an electron beam accelerator. Since the sterilizing mechanism of the electron beam is widely known, a detailed description thereof will be omitted.

The method according to the present embodiment further includes operation S10 in which inorganic matter, such as iron (Fe) and aluminium (Al), is removed from the soil in order to make the soil more suitable for growing Korean ginseng and/or operation S30 in which antagonistic rhizobacteria are supplied to the soil in order to prevent Korean ginseng from having diseases and promote the growth of the Korean ginseng.

Specifically, in operation S10, inorganic matter, such as Fe and Al, is removed from the soil since it provides nutrients to fungi harmful to ginseng and thus promotes the activity of the harmful fungi. That is, operation S10 is for removing inorganic matter from the soil.

In operation S30, antagonistic rhizobacteria, which prevent disease in ginseng by suppressing the activity of soil pathogens and facilitate the growth of ginseng, are supplied to the soil.

In the present embodiment illustrated in FIG. 1, operations S10 through S30 must be sequentially performed on the soil while the soil is being transferred at a predetermined speed by soil-transfer equipment such as a conveyor. Here, inorganic matter, in particular Fe and Al can be removed from the soil by a magnetic force.

Antagonistic rhizobacteria used to prevent ginseng from having diseases can include dominant bacteria or aseron or a mixture of the two. In addition, materials to be used as strains of antagonistic rhizobacteria can include a mixture of one or more of sawdust, rice bran, sesame dregs, powdered bones, fish meal, wheat bran, zeolite, glucose, CaO and $Na_2CO_3$.

An electron beam can be directly applied to a ginseng field by using a portable electron beam irradiator. However, it is very hard to apply the electron beam to the ginseng field by using the portable electron beam irradiator since the ginseng field is already planted with ginseng and equipped with sun shading equipment. Furthermore, ginseng fields are not level nor standardized. Hence, it is hardly efficient to apply the electron beam directly to the ginseng field while carrying the portable electron beam irradiator, considering the efforts made to do so. In this regard, it is far more efficient to take the soil away from the ginseng field after ginseng was cultivated and harvested, to sterilize the soil and bring the sterilized soil under cultivation of ginseng as in the present invention.

In order to sterilize soil for growing ginseng while transferring the soil at a predetermined speed, a transfer equipment, such as a conveyor, is used. Specifically, a predetermined amount of soil must be loaded onto the conveyor to a predetermined height and then continuously transferred by it. While the soil is being transferred, operations S10 through S30 described above must be performed on the soil. That is, inorganic matter can be removed from the soil, an electron beam must be applied to the soil, and antagonistic rhizobacteria should be supplied to the sterilized soil.

In addition, in order to transfer a fixed amount of soil, a predetermined amount of soil is continuously spread onto the conveyor to a predetermined height.

The configuration and operation of a system for sterilizing the soil for growing Korean ginseng by using an electron beam according to an exemplary embodiment of the present invention can be described with reference to FIG. 2.

Figure 2:
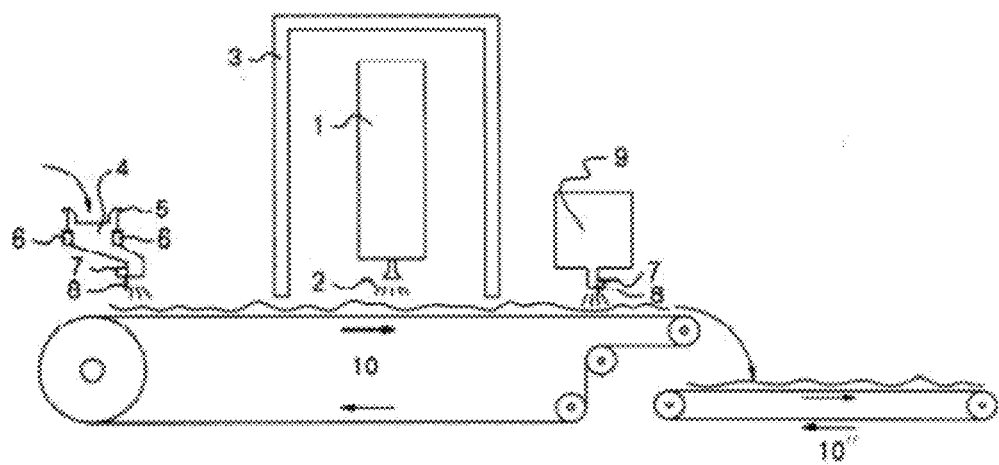

FIG. 2 is a schematic diagram of a process for sterilizing the soil for growing Korean ginseng by using an electron beam according to an exemplary embodiment of the present invention. Referring to FIG. 2, the process according to the present embodiment includes a main conveyor 10 which transfers soil at a predetermined speed, a soil supplier 4 which loads a predetermined amount of soil onto the main conveyor 10 to a predetermined height, and inorganic matter removers 6 which remove inorganic matter from soil. In addition, the process includes an electron beam irradiator 1 which applies an electron beam 2 to soil being transferred by the main conveyor 10 and eliminates fungi from the soil and an antagonistic rhizobacteria supplier 9 which supplies microbes to the sterilized soil.

Soil used in the present invention can be obtained from a first cultivated land where ginseng has never been grown or from a continuously cultivated land where ginseng has already been grown.

When soil is obtained from the continuously cultivated land where ginseng was grown once, it must be sterilized and then the sterilized soil can be brought under cultivation of ginseng in the same land. Thus, it is possible to continuously grow ginseng in the continuously cultivated land, which was not possible before.

Soil that is sterilized according to the present invention must be evenly sprinkled over ginseng beds in a ginseng field to a height of approximately 30 to 50 cm in consideration of the length of ginseng roots.

The process according to the present embodiment uses the main conveyor 10 as a unit for continuously supplying a predetermined amount of soil. That is, the inorganic matter removers 6 remove inorganic matter, such as Fe and Al, after filtering through the filter screen 5 in the soil supplier 4. Then, the soil having the inorganic matter removed is loaded onto and transferred by the main conveyor 10. While the soil is being transferred by the main conveyor 10, the electron beam irradiator 1 disposed above the main conveyor 10 applies the electron beam 2 to the soil, thereby eliminating harmful fungi from the soil. As the soil sterilized by electron beam passes through the antagonistic rhizobacteria supplier 9, antagonistic rhizobacteria helpful for the growth of ginseng are added to the soil.

Figure 3:
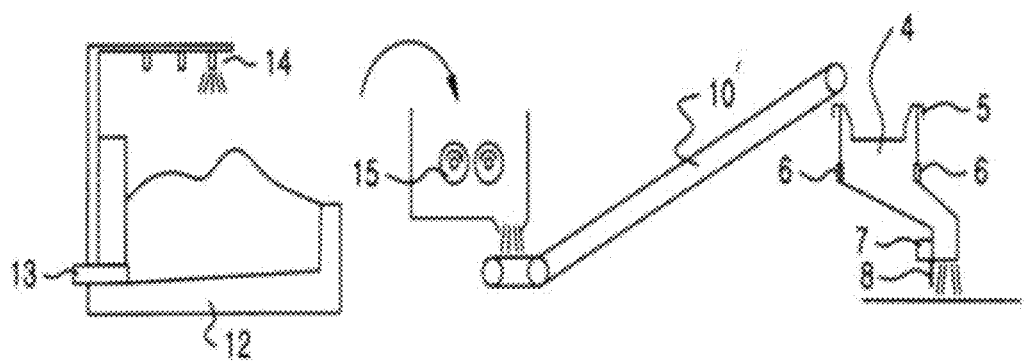
FIG. 3 is a schematic diagram of equipment for supplying soil for sterilization according to an exemplary 1st example.

In order to continuously supply soil to the soil supplier 4, a salt removing tank 12 filled with soil should be installed in front of the soil supplier 4 as shown in FIG. 3. In addition, a sprinkler 14 can be installed above the salt removing tank 12 to spray water. Water sprayed by the sprinkler 14 can dissolve salts in soil and drains through a drain 13.

Soil having salts removed as described above will be prepared by a soil grinder 15 to pass the screen to produce a predetermined amount of soil with a predetermined grain size and then transferred to the soil supplier 4 by a soil supply conveyor 10.

As described above, in the present invention, the inorganic matter removers 6 are installed to remove inorganic matter, such as Fe and Al, from soil before an electron beam is applied to the soil. Specifically, the inorganic matter removers 6 can be made of electromagnets to attract and to remove Fe and Al from soil by using their magnetic forces. The inorganic mater removers 6 made of electromagnets can be installed on both sides of the soil supplier 4.

In an upper part of the soil supplier 4, a screen 5 which is shaped like a wire net can be installed to filter soil. Specifically, the screen 5 can eliminate foreign matter from soil and allow grains of less than a predetermined size to pass there through. In a lower part of the soil supplier 4, an electric motor 7 and a switch valve 8 can be installed to control the amount of soil that is loaded onto the main conveyor 10.

The electric motor 7 can be a brushless direct current (DC) motor which does not generate mechanical nor electrical noise. The electric motor 7 must open or close the switch valve 8 according to a preset speed of the main conveyor 10, so that a predetermined amount of soil can be continuously loaded onto the main conveyor 10 to a predetermined height.

Once a predetermined amount of soil is loaded by the soil supplier 4 onto the conveyor 10 to a predetermined height, it is transferred by the main conveyor 10. While the predetermined amount of soil is being transferred by the main conveyor 10, it is sterilized by the electron beam irradiator 1 of FIG. 2.

The electron beam irradiator 1 must be covered by a safety cover wall 3. Here, a lower end of the safety cover wall 3 must be separated from the main conveyor 10 by a predetermined gap, so that soil on the main conveyor 10 can be smoothly transferred without being interrupted by the safety cover wall 3. The safety cover wall 3 is designed to protect workers from the possible harmful effects of the electron beam 2.

When the electron beam 2 emitted from an electron beam irradiator of the electron beam accelerator 1 is applied to soil being transferred by the main conveyor 10 at a predetermined speed, harmful fungi and bacteria in the soil are killed.

According to the present invention we can use an electron beam accelerator with capacity approximately 0.4 to 10 MeV to generate at least 10 kilograys (kGy) of electron beam irradiation. To increase the dose of electron beam irradiation, the capacity of the electronic beam accelerator must be also increased. Thus, it can be economical to maintain the dose of electron beam irradiation at 10 to 30 kGy.

The soil depth that is transferred by the main conveyor 10 can vary according to the irradiation capacity of the electron beam irradiator 1. Preferably, the height of the soil must be equal to or less than 5 cm, because the energy of the electron beam 2 must be significantly increased when the height of the soil is greater than 5 cm.

According to the present invention, antagonistic rhizobacteria helpful for the growth of ginseng should be added to the sterilized soil. To this end, the antagonistic rhizobacteria supplier 9 can be arranged behind the electron beam irradiator 1.

Figure 4:
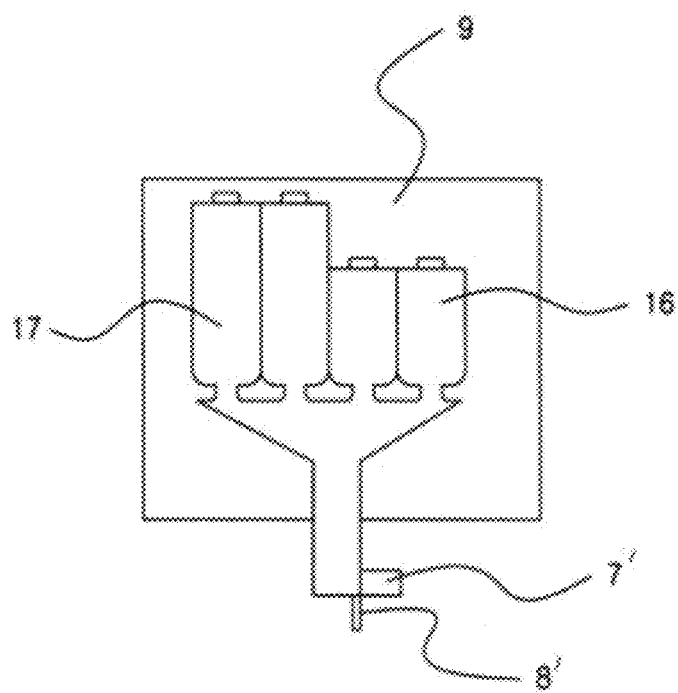
FIG. 4 is a schematic diagram of equipment for adding antagonistic rhizobacteria to the soil for growing Korean according to an exemplary 1st example.

Referring to FIG. 2 and FIG. 4, the antagonistic rhizobacteria supplier 9 includes one or more antagonistic rhizobacteria supply tanks 16, an electric motor 7', and a switch valve 8'. The electric motor 7' and the switch valve 8' are disposed under the antagonistic rhizobacteria supply tanks 16 to supply a predetermined amount of microbes to the sterilized soil. The electric motor 7' and the switch valve 8' can be identical to the electric motor 7 and the switch valve 8 of the soil suppler 4 described above.

As described above, examples of antagonistic rhizobacteria used in the present invention can include dominant bacteria or aseron or a mixture of them. In addition, materials to be used as strains of the antagonistic rhizobacteria can include a mixture of one or more of sawdust, rice bran, sesame dregs, powdered bones, fish meal, wheat bran, zeolite, glucose, CaO and $Na_2CO_3$.

The antagonistic rhizobacteria can prevent disease and promote anti-oxidation due to their antagonistic action in the soil. Since the antagonistic rhizobacteria have excellent antagonistic properties, they are highly resistant to various pathogens. In addition, the antagonistic rhizobacteria can strongly suppress various diseases due to their superior efficacy. Even when not exposed to sufficient sunlight, the antagonistic rhizobacteria can provide photosynthesis to themselves to promote their growth. The antagonistic rhizobacteria live on harmful microbes, and their secretions are used to proliferate useful microbes such as lactobacilli. Thus, the antagonistic rhizobacteria are very helpful for the growth of ginseng.

Figure 5:
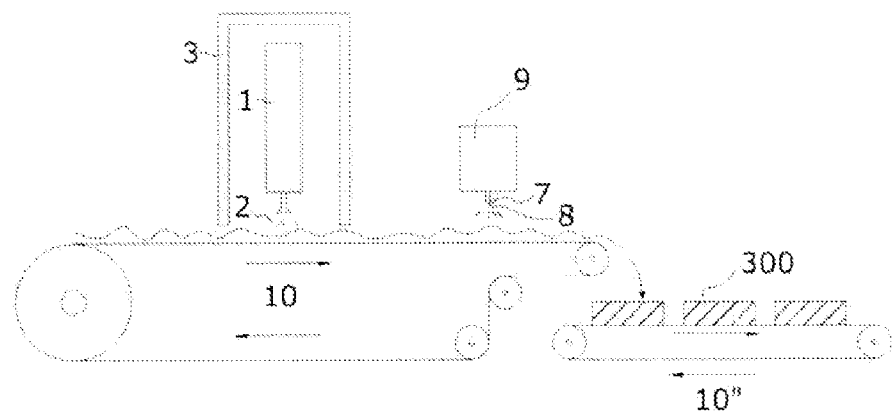
FIG. 5 is a schematic diagram of cultivation system for Korean ginseng cultivation according to an exemplary 2nd example.

Sterilized soil to which antagonistic rhizobacteria have been added by the antagonistic rhizobacteria supplier 9 is transferred to the required locations by a soil transferring conveyor 10" and guide rail as shown in FIGS. 2 and 5.

A case where the method and system according to the present invention are applied to the soil for growing ginseng has been described above. However, the present invention is not limited thereto, and various modifications will be made without departing from the technical spirit of the present invention. That is, the method and system according to the present invention can also be applied to the soil for growing other crops, in particular, medicinal plants, hardy plants, and crops such as strawberry and chilli that cannot be continuously grown in the same land.

Subsequently we explain an example of electron beam experiments.

An embodiment of the present invention will now be described. Experiments were conducted to identify whether *cylindrocarpon destructans* (*C. destructans*), which causes ginseng roots to rot, can be eliminated by using an electron beam according to the present invention. In these experiments, soil having *C. destructans* was exposed to an electron beam, and then its DNA was analysed to determine whether *C. destructans* was eliminated.

Here, the soil was irradiated at 5, 10, 15, 20 and 30 kGy. In addition, changes were observed while varying the height (thickness) of the soil for each dose of electron beam irradiation in order to determine the effects of the height of the soil. The results of the above experiments are shown in Table 1.

TABLE 1

| Experiment | Dose of Electron Beam Irradiation (kGy) | Height of Soil (cm) | Sterilization Result |
|---|---|---|---|
| 1 | 5 | 0.5 | X |
|  |  | 1 | X |
|  |  | 3 | X |
|  |  | 5 | X |
|  |  | 7 | X |
| 2 | 10 | 0.5 | O |
|  |  | 1 | O |
|  |  | 3 | O |
|  |  | 5 | O |
|  |  | 7 | X |
|  |  | 9 | X |
| 3 | 15 | 1 | O |
|  |  | 3 | O |
|  |  | 5 | O |
|  |  | 7 | X |
|  |  | 9 | X |
| 4 | 20 | 1 | O |
|  |  | 3 | O |
|  |  | 5 | O |
|  |  | 7 | X |
|  |  | 9 | X |
| 5 | 30 | 1 | O |
|  |  | 3 | O |
|  |  | 5 | O |
|  |  | 7 | X |
|  |  | 9 | X |

As shown in Table 1, when exposed to less than 10 kGy of electron beam irradiation, *C. destructans* was not eliminated. However, *C. destructans* was eliminated when irradiated at a dose of more than 10 kGy and at soil depth of less than 5 cm. In addition, *C. desctructans* was more easily eliminated when the energy of the electron beam was far more than 10 kGy.

In polymerase chain reaction (PCR) that followed electron beam irradiation, C. destructans was eliminated 100% when irradiated at a dose of 10 kGy or above, regardless of whether *C. destructans* was contained in the soil from a first cultivated land where Korean ginseng has never been grown or in the soil from a continuously cultivated land where Korean ginseng was grown once and therefore contains a greater amount of *C. destructans* than the first cultivated land.

PCR refers to a technique of amplifying a desired DNA molecule in a test tube by repeatedly synthesizing a specific part of DNA. In the above experiments, *C. destructans*, which causes root to rot, was detected directly from ginseng by using the PCR technique.

According to the experiments, *C. destructans*, which is a major cause of root rots of ginseng, was not eliminated at a small dose of electron beam irradiation. It was determined that we need a dose of electron beam at least 10 kGy to eliminate C. destructans.

The growth of ginseng in soil, which was sterilized by electron beam irradiation, was also compared with that of ginseng in un-sterilized soil. The results of comparison showed that ginseng grew 1.2 times bigger in the sterilized soil than in the un-sterilized soil, regardless of whether the sterilized soil was obtained from the first cultivated land or the continuously cultivated land. That is, it was proved that sterilized soil with an electron beam is effective for the growth of ginseng.

This 2nd example is a cultivation system of Korean ginseng to grow effectively using the sterilized soil through the above-mentioned 1st example of design.

Figure 6:
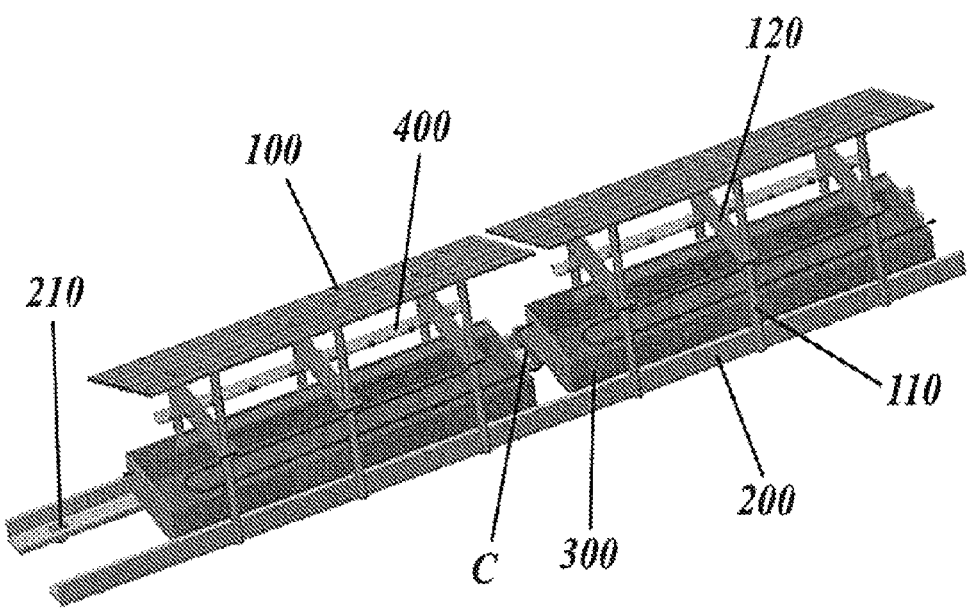
FIG. 6 is a schematic picture of ginseng-field-modules' assembly according to an exemplary 2nd example.
Figure 7:
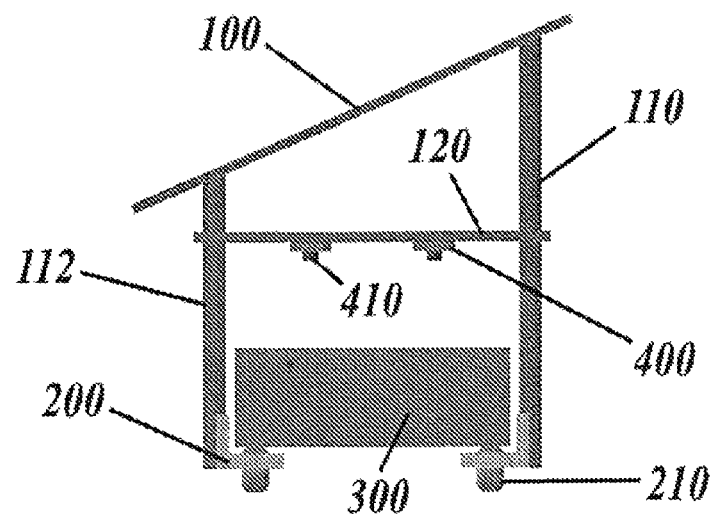
FIGS. 7 to 9 are schematic front view, side view and diagonal view of ginseng-field-modules' assembly according to an exemplary 2nd example.
Figure 8:
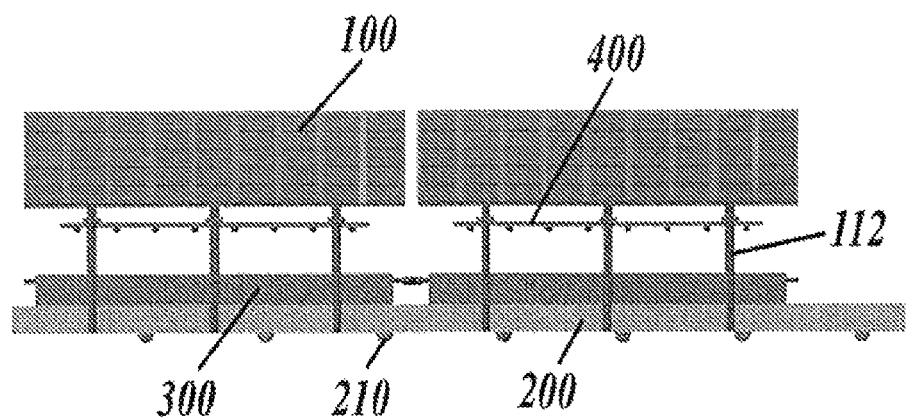
Figure 9:
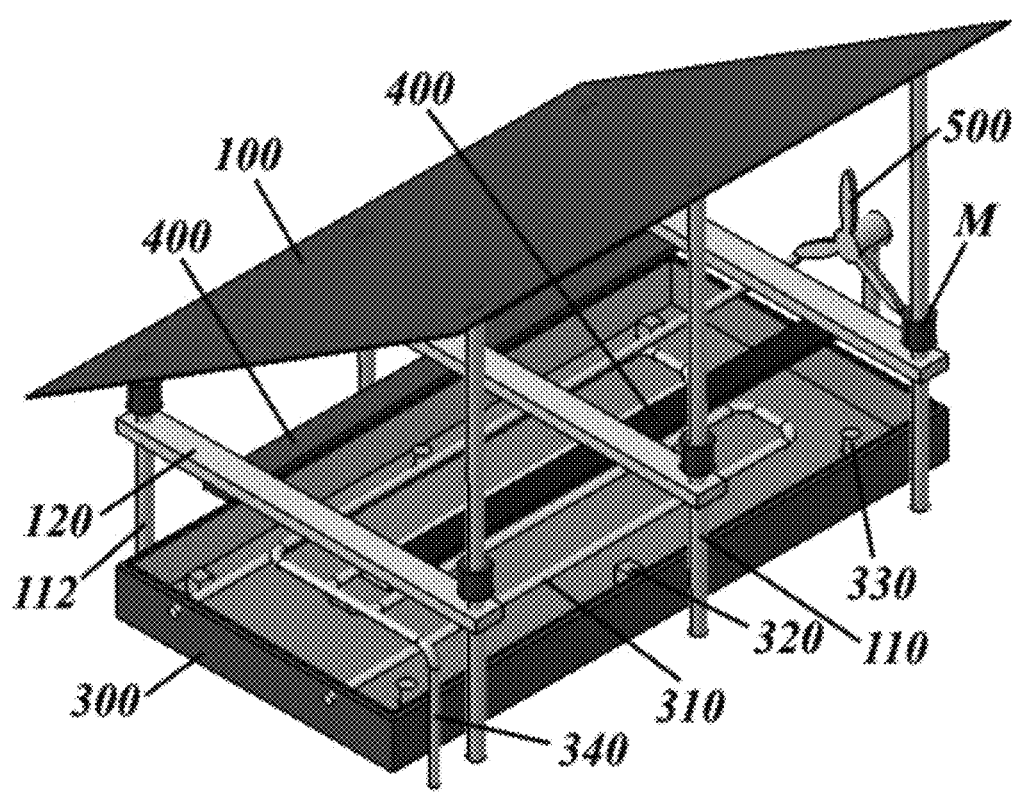

FIG. 5 is a schematic diagram of cultivation system of Korean ginseng according to the present invention. FIG. 6 is an exemplary view of a ginseng-field-module's assembly according to the present invention. FIG. 7 is exemplary side view of a ginseng-field-module's assembly according to the present invention. FIG. 8 is exemplary front view of a ginseng-field-module's assembly according to the present invention. FIG. 9 is exemplary diagonal view of a ginseng-field-module's assembly according to the present invention.

If we refer to FIG. 5 and FIG. 6, the cultivation system of Korean ginseng according to the 2nd example consists of main conveyor(10), electron beam accelerator(1), inorganic matter remover(6), antagonistic rhizobacteria supplier(9), salt removing tank(12) and ginseng-field-module's assembly filled with the sterilized soil and arranged at the back of solar cell panels(100) in a solar cell yard using the sterilized soil through the above-mentioned 1st example of design.

Such a ginseng-field-module's assembly consists of ginseng-field-modules(300) filled with the sterilized soil, solar cell panel(100) and guide rail(200) through which ginseng-field-modules can be transported.

Like FIG. 6 or FIG. 9, ginseng-field-modules(300) are set through guide rail(200) on the shade place between solar cell panels(100) installed using beams(110,112) and support posts(120).

The above-mentioned guide rail(200) has L-profile and many wheels with a certain distance on the L-profile. Because of wheels on guide rail's L-profile ginseng-field-modules can be easily slid to ginseng field through the guide rail(200). The guide rail can be easily assembled or disassembled by bolts. This guide rail(200) connects conveyor(10") and a ginseng field or the shading place of solar cell panels in a solar cell yard.

A ginseng-field-module(300) is a rectangular box filled with the sterilized soil according to the 1st example. We usually use a pipe with small holes to supply ginseng field water or nourishment. Therefore we install a injection pipe (310) with many curves at the top of the ginseng-field-module (300).

In this case, we provide the nourishment EC with a concentration 0.5 dS/m or 1.0 dS/m two times pro a month. The PH(Potential Hydrogen) of nourishment must be adjusted 5.0~6.0 using $H_2SO_4$ and KOH.

TABLE 2

| Element/Composition | Nourishment EC with Concentration (dS/m) | |
|---|---|---|
| $Ca(NO_3)_2 4H_2O$ | 93.9 | 187.0 |
| $KNO_3$ | 50.6 | 101.1 |
| $NH_4NO_3$ | 8.0 | 16.0 |

TABLE 2-continued

| Element/Composition | Nourishment EC with Concentration (dS/m) | |
|---|---|---|
| $MgSO_4 7H_2O$ | 49.2 | 98.4 |
| $KH_2PO_4$ | 13.6 | 27.1 |
| Fe-EDTA | 2.0 | 4.0 |
| $H_3BO_3$ | 0.3 | 0.5 |
| $ZnSO_4 4H_2O$ | 0.02 | 0.04 |
| $CuSO_4 4H_2O$ | 0.005 | 0.01 |
| $NaMoO_4 2H_2O$ | 0.02 | 0.04 |

And temperature—and humidity sensor(320, 330) are installed in the inside of the ginseng-field-module(300), so that we can keep optimal temperature and humidity of ginseng field through these sensors.

Another sprinkler(340) can be installed above ginseng-field-module(300), in order to supply water or to spray environment-friendly plant protecting agent.

Each ginseng-field-module(300) can be connected in a straight line or in layer upon layer by clip-coupling-pipes(C) and a rack. Injection pipe(310) of each ginseng-field-module (300) is also connected with neighboring one by this clip-coupling-pipe(C).

On the support post(120) are installed two LED-mounting plates(400) on which blue—and red LEDs(410) are attached. Therefore if there is no sufficient sun light, for example on a cloudy day or in rainy season, we can activate ginseng's photosynthesis using these LEDs(410). In order to activate the photosynthesis of ginseng we normally use blue—and red LEDs(410).

And a fan can be installed by the side of ginseng-field-module(300) to keep temperature of ginseng field or ginseng-field-module(300) from 20 to 27 in summer.

In the following, we give an amplification of the effect of blue—and red LED lighting(410). This blue—and red LED lighting activates ginseng's photosynthesis. Photosynthesis is the process by which plants use the energy from sunlight to produce sugar.

The conversion of unusable sunlight energy into usable chemical energy is associated with the actions of the green pigment chlorophyll. Photosynthetic process uses water and carbon dioxide and then releases the oxygen. We can write the reaction of this process as:

$$6CO_2 + 12H_2O + Light \longrightarrow C_6H_{12}O_6 + 6H_2O + 6O_2$$

or $$6CO_2 + 6H_2O \xrightarrow{h\nu}_{chlorophyll} C_6H_{12}O_6 + 6O_2$$

At this time, if we look at the two equations, we can find that light energy in the range of visible ray activates the chemical reaction of green plant. If we monitor photosynthesis of green plant, we can see that the curve of carbon dioxide absorption has maximum value at blue—and red range from visible ray spectrum.

In other words, green plant absorbs the maximum carbon dioxide from air at blue—and red visible ray and produces the maximum grape sugar and oxygen in proportion to the amount of absorbed carbon dioxide. Therefore, if we can control blue—and red LED lighting to light Korean ginseng, its lighting time and intensity of lighting, that is, if we control blue—and red visible ray, the flower season or amount of crop can be adjusted, because the time and intensity of photosynthesis are controlled. In the present invention, blue—and red LEDs(410) are installed in the ginseng-field-module(300) to support ginseng's photosynthesis in cloudy weather or rainy season. Therefore, we can light blue LED($\lambda$=470 nm) or red LED($\lambda$.32 650 nm) on ginseng field or ginseng-field-module (300) not only to bring higher productivity of ginseng but also to produce higher-quality one with more content of saponins and other elements.

In addition, the electrical motor(M) of the beam(110,112) in FIG. 4 can lengthen or backtrack the beam(110,112) like a antenna, in order to optimize the angle of the solar cell panel (100) according to the Sun's movement or in a storm and heavy snowfall.

The 2nd example of the present patent has linked process with each other for this. The sterilized soil for growing Korean ginseng according to the 1st example is transported direct to ginseng field or loaded into the ginseng-field-module(300) located on the conveyor(10"). And the ginseng-field-module(300) filled with the sterilized soil can be transported to the shading place in the back of the solar cell panels in a solar cell yard. Each ginseng-field-module(300) can be connected in a straight line or in layer upon layer by clip-coupling-pipes(C) and a rack considering each solar cell yard and its geographical condition. If we arrange ginseng-field-modules(300) in layer upon layer- multi story frames, we can mass-produce ginseng from a small-scale farmland. Injection pipe(310) of each ginseng-field-module(300) is also connected with neighboring one by this clip-coupling-pipe(C).

The temperature and humidity of ginseng-field-modules (300) are continuously monitored and controlled by each sensor(320, 330), fan (500) and pipe with small holes (310), in order to keep an optimal condition for ginseng's growth and development.

According to the present invention, an electron beam is applied to soil to eliminate fungi harmful to ginseng's growth and development, and then the sterilized soil is used to grow ginseng. Therefore, various diseases caused by the fungi can be prevented, so that thus high-quality Korean ginseng can be grown in the soil.

In addition, after ginseng is harvested from the soil, the electron beam is applied again to the soil to eliminate fungi. And then the sterilized soil is used to construct ginseng beds in a ginseng field or to be filled into ginseng-field-modules. Therefore, the soil can be reused to continuously grow Korean ginseng through the electron beam irradiation.

In the present invention, inorganic matter and fungi harmful to ginseng are removed from soil, while antagonistic rhizobacteria helpful for the growth of ginseng are added to the soil. Therefore, optimal soil for growing high-quality ginseng can be made through electron beam irradiation and supply of antagonistic rhizobacteria.

Since the present invention makes it possible to grow ginseng continuously and organically in the same land, the efficiency of land use can be maximized, and the incomes of farming households can be increased.

A method and system for sterilizing soil according to the present invention can be applied not only to ginseng but also to value-added medicinal plants, hardy plants, and other crops such as strawberry and chili that cannot be continuously grown in the same land.

Because ginseng-field-module is one unit, we can assemble each ginseng-field-module in a straight line or in layer upon layer by clip-coupling-pipes and a rack considering geographical condition for a more optimal ginseng field.

We can collect data for temperature and humidity of ginseng-field-modules through its sensor and control the temperature and humidity of them, so that we can take measures to produce high-quality Korean ginseng with uniform quality.

We can also activate ginseng's photosynthesis using blue—and red LED lighting in cloudy weather or rainy season, in other words in all weather condition.

What is claimed is:

1. A System for cultivation of Korean ginseng using a soil sterilized by an electron beam, the system comprising:
    a soil supplier which prepares and screens the soil for growing Korean ginseng and loads this soil on a conveyor in predetermined amounts;
    a salt removing tank which is disposed in front of the soil supplier, said tank including a drain in a lower part thereof;
    a sprinkler which is disposed above the salt removing tank and sprays water over the soil for growing Korean ginseng;
    a main conveyor which transfers the soil for growing Korean ginseng supplied by the soil supplier at a predetermined speed;
    an electron beam irradiator which applies an electron beam to the soil for growing Korean ginseng being transferred by the main conveyor to eliminate harmful fungi contained in the soil for growing Korean ginseng;
    a conveyor located at the end of the main conveyor;
    a ginseng-field-module is filled with the sterilized soil for growing Korean ginseng and transported to a guide rail on the conveyor;
    a plurality of solar cell panels; and
    the guide rail transports the ginseng-field-module from the end of the conveyor to a back side of the solar cell panels in a solar cell yard or in a sun shading place in a ginseng field.

2. The system of claim 1, wherein a plurality of the ginseng-field modules are assembled in a straight line or in multi-layer form by clip-coupling-pipes and a rack under solar cell panels in the solar yard or the sun shading place in a ginseng field.

3. The system of claim 1, wherein a pipe with small holes is installed inside of the ginseng-field-module to supply the filled soil for growing ginseng water or nourishment.

4. The system of claim 1, wherein the ginseng-field-module includes a temperature sensor and a humidity sensor.

5. The system of claim 1, wherein blue- and red LEDs are installed above the ginseng-field-module to support ginseng's photosynthesis in cloudy weather or rainy season.

6. The system of claim 1, wherein the ginseng-field-modules further comprises fans to optimize temperature and humidity for ginseng's growth and development.

7. The system of claim 1, wherein the soil supplier comprises an electromagnet which removes inorganic matter from the soil for growing Korean ginseng.

8. The system of claim 1, further comprising an antagonistic rhizobacteria supplier which is disposed at an end of the main conveyor behind the electron beam irradiator and which adds antagonistic rhizobacteria to the soil for growing Korean ginseng sterilized by using the electron beam.

* * * * *